US009023005B2

(12) United States Patent
Vasic (10) Patent No.: US 9,023,005 B2
(45) Date of Patent: May 5, 2015

(54) DISPOSABLE ABSORBENT ARTICLE HAVING A BARRIER (75) Inventor: Dragorad Vasic, Bollebygd (SE)

(73) Assignee: SCA Hygiene Products AB, Gothenburg (SE)

( * ) Notice: Subject to any disclaimer, the term of this patent is extended or adjusted under 35 U.S.C. 154(b) by 525 days.

(21) Appl. No.: 13/320,139

(22) PCT Filed: May 12, 2009

(86) PCT No.: PCT/SE2009/050528
§ 371 (c)(1),
(2), (4) Date: Nov. 11, 2011

(87) PCT Pub. No.: WO2010/132000
PCT Pub. Date: Nov. 18, 2010

(65) Prior Publication Data
US 2012/0071851 A1    Mar. 22, 2012

(51) Int. Cl.
A61F 13/475    (2006.01)
A61F 13/49     (2006.01)
A61F 13/15     (2006.01)
A61F 13/494    (2006.01)

(52) U.S. Cl.
CPC ..... A61F 13/15739 (2013.01); A61F 13/15756 (2013.01); A61F 13/49014 (2013.01); A61F 13/49413 (2013.01); A61F 13/4942 (2013.01)

(58) Field of Classification Search
USPC .......................................... 604/385.28, 389
See application file for complete search history.

(56) References Cited

U.S. PATENT DOCUMENTS 5,331,683 A * 7/1994 Stone et al. ................ 2/2.5
5,429,632 A * 7/1995 Tanji et al. ............... 604/385.28
5,599,338 A   2/1997 Enloe
5,624,426 A   4/1997 Roe et al.

(Continued)

FOREIGN PATENT DOCUMENTS

CN    8043276     7/2008
EP    0 311 333   4/1989

(Continued)

OTHER PUBLICATIONS

Decision on Grant dated Oct. 9, 2012 from corresponding Russian patent application No. 2011150251 (12 pages).

(Continued)

*Primary Examiner* — Susan Su
(74) *Attorney, Agent, or Firm* — Drinker Biddle & Reath LLP (57) ABSTRACT

A disposable absorbent article having at least one barrier at least one barrier extending along at least a longitudinal side of the crotch portion having a proximal end being connected to the remains of the article and a distal end forming a longitudinally extending free edge. At least one of the front and rear portion have a side portion extending transversely outwardly of the proximal end of the barrier to a side portion end for fastening to the other of the front and rear portion, so as to form a closed position of the article defining a leg opening. A connecting member connects the barrier with the side portion, and extends between a first connection where the connection member is connected to the barrier and a second connection where the connection member is connected to the side portion, such that when the side portion is subject to a traction force, the traction force will be at least partially transferred to the barrier via the connecting member.

20 Claims, 5 Drawing Sheets

(56) References Cited

U.S. PATENT DOCUMENTS

| | | | |
|---|---|---|---|
| 5,674,213 A * | 10/1997 | Sauer | 604/385.01 |
| 5,899,895 A * | 5/1999 | Robles et al. | 604/385.29 |
| 5,997,521 A * | 12/1999 | Robles et al. | 604/385.22 |
| 6,406,465 B1 * | 6/2002 | Otsubo | 604/385.01 |
| 6,413,249 B1 * | 7/2002 | Turi et al. | 604/387 |
| 6,641,570 B2 * | 11/2003 | Mishima et al. | 604/385.28 |
| 6,790,203 B2 * | 9/2004 | Een | 604/385.28 |
| 8,043,276 B2 | 10/2011 | Suzuki et al. | |
| 2002/0143313 A1 * | 10/2002 | Tsuji et al. | 604/385.03 |
| 2003/0040731 A1 * | 2/2003 | Nozaki et al. | 604/385.28 |
| 2003/0216704 A1 | 11/2003 | George | |
| 2004/0059311 A1 | 3/2004 | Minato et al. | |
| 2004/0133181 A1 | 7/2004 | Ishiguro et al. | |
| 2004/0215161 A1 * | 10/2004 | Okuda et al. | 604/385.28 |
| 2006/0047259 A1 * | 3/2006 | Erdman et al. | 604/389 |
| 2006/0100601 A1 * | 5/2006 | O'Connell | 604/389 |
| 2007/0191806 A1 * | 8/2007 | Mueller et al. | 604/385.19 |
| 2008/0132863 A1 * | 6/2008 | Waksmundzki et al. | 604/367 |
| 2008/0312631 A1 * | 12/2008 | Okuda | 604/385.23 |
| 2009/0299318 A1 * | 12/2009 | Faulks et al. | 604/385.03 |

FOREIGN PATENT DOCUMENTS

| | | |
|---|---|---|
| EP | 0913137 | 5/1999 |
| EP | 1 023 883 | 8/2000 |
| EP | 1 035 818 | 4/2002 |
| GB | 2284538 | 6/1995 |
| JP | 4-295356 | 10/1992 |
| JP | 2003-079659 | 3/2003 |
| JP | 2003079659 A * | 3/2003 |
| RU | 2179008 | 2/2002 |
| WO | 02/49560 | 6/2002 |
| WO | 2007/139454 | 12/2007 |

OTHER PUBLICATIONS

Extended European Search Report dated Jul. 25, 2013 issued in corresponding European patent application No. 09844711.3 (6 pages).

* cited by examiner

DISPOSABLE ABSORBENT ARTICLE HAVING A BARRIER

CROSS-REFERENCE TO PRIOR APPLICATION

This application is a §371 National Stage Application of PCT International Application No. PCT/SE2009/050528 filed May 12, 2009, which is incorporated herein in its entirety.

TECHNICAL FIELD

The present disclosure relates to a disposable absorbent article intended to be worn around the waist of a user. Such articles include, for example, child and adult diapers, training pants, pull-up diapers, adult incontinence pants, and swim pants. In particular, the disclosure relates to a disposable absorbent article having at least one barrier extending along at least a longitudinal side of a crotch portion of the article, the barrier having an proximal end, extending in the longitudinal direction. The proximal end is associated with the top side of the article, and a distal end extends in the longitudinal direction.

The disclosure further relates to a method of manufacturing such a disposable absorbent article.

BACKGROUND

As well as good absorptive properties, primary requirements of absorbent articles are good fit and comfort coupled with the need to prevent leakage of any received bodily waste. To this effect, contemporary absorbent articles are provided with elastically extensible regions around the leg openings to thereby create a gusset around each leg when the article is worn.

However, to furthermore increase security against leakage, contemporary absorbent articles are often provided with so called barriers, preferably extending inside of the elastically extensible regions around the leg openings, along the crotch portion of the article. The barriers are intended to form a first hinder against leakage, in order to keep the bodily waste in the centre of the article and preferably away from the leg openings.

Another measure for increasing the fit and hence the security of absorbent articles is the provision of side portions made from elastically extensible material.

The manufacture of an article having barriers for preventing sideway leakage is described e.g. in WO 2007/139454, U.S. Pat. No. 5,599,338, WO 2002/049 560 or EP 1 023 883.

The barriers are in general very efficient when in comes to inhibiting leakage. However, their function relies on the barriers being properly positioned so as to form the desired hinders against leakage. If the barriers are inhibited from assuming their intended position, e.g. if they become improperly folded during pull-up of the article, their function as barriers is severely impaired. To ensure correct positioning of the barriers, the person changing the article might wish to verify the position of the barriers via the leg openings.

Moreover, even if the barriers are initially correctly positioned, they may be removed from the correct position during use of the article, e.g. become depressed while the article is worn.

In view of the above, there is a need for an article having barriers, wherein the ability of the barriers to automatically assume and/or maintain a correct, upstanding position when the article is worn, is improved.

Moreover, there is a need for an article providing improved resistance against leakage.

SUMMARY

It is desired to provide an absorbent article which fulfils at least one of the above-mentioned needs.

The above-mentioned can be achieved by a disposable absorbent article intended to be worn around the waist of a user, such as a diaper or an incontinence article. The article extends in a longitudinal direction about a longitudinal axis and in a transverse direction about a transverse axis. The article includes a front portion, a rear portion and an intermediate crotch portion. The article includes a liquid-permeable top side, and a liquid-impermeable back side. The article has at least one barrier extending along at least a longitudinal side of the crotch portion. The barrier has a proximal end, extending in the longitudinal direction, the proximal end being connected to the remains of the article, and a distal end extending in the longitudinal direction, the distal end forming a longitudinally extending free edge. At least one of the front and rear portions have a side portion, extending transversely outwardly of the proximal end of the barrier to a side portion end for fastening to the other of the front and rear portion, so as to form a closed position of the article defining a leg opening. The article further includes a connecting member, which connects the barrier with the side portion. To this end, the connecting member extends between a first connection where the connection member is connected to the barrier, the first connection being located at a distance from the proximal end of the barrier, and a second connection where the connection member is connected to the side portion, such that when the side portion is subject to a traction force, such as when the article is applied or worn, the traction force will be at least partially transferred to the barrier via the connecting member.

When the article as described above is applied to a wearer, or while it is worn, the side portion will typically be subject to traction forces. Such forces arise e.g. by a user pulling the sides of the article for applying it to a wearer, or by the movements of the wearer when the article is worn. The traction forces applied to the side portion will at least partially be transferred to the connecting member, and then in turn to the barrier. The traction force being transferred to the barrier at some distance from the proximal end thereof (the proximal end is fastened to the remains of the article) will promote drawing the barrier out, which is advantageous in order to tighten the connecting member towards the wearer, whereby the risk of leakage is diminished. In particular, the drawing out of the barrier may contribute to rising the barrier towards an erected position, and to maintain it in the position.

The connecting member extends between the first and the second connection, i. e. the connection member extends freely between the first and the second connection. The connection member could be connected to the side portion and/or to the barrier at additional connections, e.g. for securing the ends of the connecting member.

It will be understood, that when the article is applied or worn, the side portions of the article may be subject to traction forces in all directions. However, the most pronounced traction forces will generally be applied in a transversally outward direction, and will act so as to draw the side portions transversally outwardly. This outward motion will be transferred via the connecting member to the barrier, which will also be drawn transversally outwards.

The barrier being drawn out means that it is at least tensioned along its length, hence that creases or wrinkles in the barrier are counteracted. The barrier being drawn out could, but need not, imply that the barrier is also elongated. The same applies for the drawing out of the side portion, and for the connecting member.

The term "connection" is to be interpreted as including joints such as made by gluing, welding, or other forms of joining two separate pieces of material. In this case, the joint may be continuous or intermittent, e.g. formed by a continuous weld line or by intermittent welded dots.

The term "connection" is also to be interpreted as including continuous connections, such as when the connection member is formed continuously with the material of the side portion or the barrier. For example, the connection member could be formed continuously with the side portion material, or with a sub-portion of the side portion. In this case, the second connection could be formed by a fold in the continuous material forming both the connection member and the side portion.

Alternatively, the connection member could be formed continuously with the barrier, or with a sub-portion of the barrier. In this case, the first connection could be formed by a transition in the material forming both the barrier and the connection member. For this alternative, it could be preferred if the connection member extends from the free end of the barrier, e.g. forming an extension from the distal end of the barrier.

However, in particular embodiments, the connection member is an individual member, which is connected to the remains of the article via connections formed by joints.

In the context of this application, the side portion is to be defined as a portion of the front or rear portion extending transversely outwardly as seen from the transversal position of the proximal end of the barrier. The side portion could be composed of one single homogenous portion, or of several subportions. Typically, the side portion could include a region of the front or rear portion of the article, including e.g. the backsheet and the topsheet. In addition, the front or rear portion of the article could be provided with side panels, extending transversely outwardly of the regions of the front or rear portion of the article. Such side panels would also form part of the side portion of the article. Hence, when discussing e.g. the stretchability of the side portion, what is referred to is the stretchability of the entire side portion, from the proximal end of the barrier to the side portion end.

As mentioned above, the connection member extends between a first connection, where it is connected to the barrier, and a second connection, where it is connected to the side portion.

For efficiently drawing out the barrier, the first connection may advantageously be located closer to the free end of the distal end of the barrier than to the proximal end. In particular embodiments, the first connection is located at the free end of the distal end itself.

The second connection may advantageously be located connecting closer to the side portion end than to the proximal end of the barrier. Accordingly, a relatively large proportion of any transversal drawing out or extension of the side portion will be transferred to the connecting member. In a particular embodiment, the second connection is located at the side portion end. This is advantageous for transfer of the transversal drawing out or extension of the side portion, and moreover enables embodiments being particularly advantageous from a manufacturing point of view.

In a particular embodiment, the side portion may be stretchable, in particular elastic.

The term "stretchable" as used herein refers to a material that may be extended, deformed or the like, without breaking. A material being stretchable means that it may or may not significantly retract after removal of an extending force.

Stretchable materials which, upon removal of an elongating force experiences a substantially permanent deformation or which does not exhibit a significant retractive force are referred to herein as "extensible".

In particular embodiments, the stretchable materials utilised may be stretched in at least one direction without breaking by at least 25% (meaning that it is stretched to at least 125% of its initial unstretched length). Suitably, the stretchable material may be stretched in at least one direction without breaking by at least 50%. The above conditions should apply at a relative humidity of about 50% and a temperature of about 23° C.

Moreover, in further particular embodiments, elastomeric materials may be stretched in at least one direction without breaking by at least 30% (meaning that it is stretched to at least 130% of its initial unstretched length), more suitable at least 50%, and which will recover, upon release of the applied stretching or biasing force, at least 10% of their elongation preferably at least 30% of their elongation. Advantageously, the elastomeric material should be capable of being elongated by at least 100% of its relaxed length and recover at least 30%, preferably at least 50%, of its elongation upon release of a stretching force, within about one minute with relative humidity about 50% and a temperature about 23° C.

As an example, a material having an initial unstretched length of 3 cm which may be stretched without breaking to a length of at least 3.75 cm in at least one direction would be a stretchable material which may be stretched by at least 25%.

In the above, the term "material" is intended to include composite materials.

Elastic materials may have a laminate structure including an interior layer and at least one additional layer disposed exteriorly of the interior layer. Anyone of the layers in the laminate structure may be of a material being elastic per se, in order to render the laminate material elastic. Suitable materials for the elastic layer are well-known and include natural rubber strands, synthetic rubber strands, elastomeric films, elastomeric nonwovens, etc. A particular laminate structure includes an interior elastic layer laminated between two exterior layers of inelastic nonwoven material.

The layers may be laminated by any method(s) suitable for attaching the layers and their constituent materials together.

For example, a stretch bonded elastic laminate may be used. In a stretch bonded elastic laminate the elastic layer may be maintained in a stretched condition while being attached to one or more non-stretched layers. When the elastic layer is released, the resulting contraction of the elastic layer will create rugosities or gathers in the non-elastic layer(s). The final laminate material may then be extended in the direction of the original stretch up to an elongation corresponding to the size of the elastic layer during attachment of the non-stretched layers thereto.

Another example of creating an elastic laminate is to gather or pleat the unstretchable layers and to attach the elastic layer thereto when unstretched. The resultant laminate may be extended in a direction perpendicular to the pleat ridges of the unstretchable layers up to the dimensions of the unstretchable layers before pleating.

The above-mentioned techniques may also be combined by pleating non-elastic layers and laminating these to an elastic material while stretching the elastic material.

Moreover, neck bonded laminates may be used. Such laminates may be formed by neck stretching a nonwoven material, and laminating the neck stretched nonwoven to an elastic layer. The laminate will be elastic in a direction perpendicular to the direction of the stretching of the nonwoven.

For laminates to be elastic both in the machine direction MD and in the cross direction CD, a laminate including a neck stretched nonwoven bonded to a stretched elastic layer or alternatively an activated laminate might be suitable.

The lamination may also be performed while both the elastic layer and the inelastic layers are relaxed. The resultant laminate or a portion thereof may thereafter be "activated" by subjecting it to elongation, whereby the inelastic layers will be torn. Activation methods which may be used include e.g. so called "ring-rolling" processes. The activation may be made in both directions of the material.

In the context of this application, a laminated material of the above-mentioned type, which is attached e.g. to the absorbent article before activation thereof, and will not strictly be elastic before activation, is nevertheless referred to as an elastic material, also before activation thereof.

As mentioned above, the side portion may in particular be elastic. This not only allows for better fit and comfort of the article, but is also particularly suitable in combination with an elastic connection member. When an article including elastic side portions is applied to a wearer or worn, the side portions will typically extend somewhat in a transverse direction. The extension will result in a traction force being transferred to the connection member, and in turn to the barrier, so as to at least draw the barrier out.

It will be understood that the entire side portion may be formed from elastic material. However, the side portion may also be formed by several materials having different elastic properties. For example, some areas of the side portion may be more elastic than other areas.

Advantageously, the side portion is rendered stretchable or elastic by the inclusion of a stretchable, in particular elastic side panel in the side portion. An elastic side panel is herein understood to be a piece of an elastic material, which is arranged to form the entire, or a part of the side portion. An elastic side panel may advantageously form an outer area of a side portion, wherein the remainder of the side portion area may be formed from an essentially inelastic material.

In a particular embodiment, the barrier may be stretchable, in which case the drawing out of the barrier could lead to the free edge of the barrier being elongated. In a more particular embodiment, the barrier may be elastic.

In particular embodiments, the connecting member is elastic at least in the transverse direction.

As will be understood from the above, that in particular embodiments, in at least one of the side portion, the connecting member and the barrier is stretchable or can be preferably elastic. It is more particular that in at least two of the side portion, the connecting member and the barrier are stretchable, or can be preferably elastic. In yet more particular embodiments, all three of them. With several stretchable or elastic parts, the interconnected side portion, connecting member and barrier may form a dynamic arrangement, where several elastic parts may expand and contract to follow the movements of a wearer. This will provide for better comfort while inhibiting leakage via the barriers.

However, other embodiments are possible. For example, the side portion may be made out of a non-stretchable material but which is longer in a transversal direction than the connection member, meaning that in a flat position, before any traction forces are applied to the side portion, the side portion forms a fold underneath the connection member. When traction forces are applied, the side portion fold may be at least partially unfolded, such that traction force will be transferred to the connection member.

Advantageously, the size and stretchability of the connecting member are selected in relation to the size and stretchability of the side portion such that, when the article is in a closed position and positioned around a wearer, both the side portion and the connecting member are stretched from their relaxed positions. Accordingly, it is ensured that both the stretchability of the side portion and the stretchability of the connecting member are active when the article is in use.

The first connection, between the connecting member and the barrier, may advantageously extend longitudinally from a first position to a second position, wherein the second position is located further away from the transverse axis than the first position.

The central-most possible location of the first position is generally determined by the presence of the leg-opening, as it will generally not be desired that the connecting member interferes with the leg opening. Hence, the first position may in particular be located adjacent to the leg opening of the article.

The second position may be located adjacent to a longitudinal beginning of the free edge of the distal end of the barrier. The barrier may conveniently be fastened to the underlying material (e.g. the topsheet), not only along the proximal end of the barrier, but also in fastening regions, for holding the barrier in an initial folded position before raising of the barriers. In the fastening regions, the barrier may be fastened to the underlying material adjacent the distal edge of the barrier. The fastening regions are suitably located at the front and/or rear portion of the article. Accordingly, the distal end of the barrier forms a free edge extending between these fastening regions, and the barrier is capable of being raised between the fastening regions. As it is desired to draw out the barrier, the first connection may advantageously start at about at the beginning of the free edge of the barrier. Accordingly, the second position may advantageously be located adjacent to a longitudinal beginning of the free edge of the distal end of the barrier.

However, in alternative embodiments, the first position may be located further away from the leg opening, towards the front and/or rear portion of the article, and/or the second position may be located further away from the beginning of the free end, towards the transversal axis of the article.

In particular embodiments, the article is of a type where, when the article is in a storage position before application of a traction force to the side portion, the distal end of the barrier is located between the longitudinal axis of the article and the longitudinal proximal end of the barrier. Hence, the connecting member will act as to draw the barrier in a direction transversely away from the longitudinal axis when the article is applied or worn.

However, the provision of a connecting member as described herein will be useful also for other cases, such as for articles where the distal end of the barrier in a storage position is located between the proximal end of the barrier and the longitudinal edge of the article.

When the article is in a storage position, the location of the distal end may conveniently be ensured by the distal end being fastened to the remains of the article in connection regions as described above.

Advantageously, the article is of the type being provided with two barriers, extending longitudinally along transversely opposite sides of the crotch portion, and where the rear or front portion is provided with two elastic side portions, provided on transversely opposite sides of the rear or front portion. Here, two connecting members may be provided to connect each barrier with the respective side portion.

For at least partially drawing out the barrier, it is sufficient that the barriers are connected to side portions via connecting members at either the front or the rear portion of the article.

However, the effect is particularly enhanced if the rear and the front portion are both provided with two side portions, and with two connecting members, such that each barrier is connected to one side portion at the rear portion of the article via a connecting member, and the same barrier is connected to another side portion at the front portion of the article via another connecting member. In this case, the stretching effect of the connecting members will be effective at both the front portion and the rear portion of the article, which will be particularly useful for drawing out the barriers.

In one variant, the article may be an open-type article. An open-type article is an article which is delivered in an open position and which forms a closed position only when fastened around the waist of a wearer. In this case, a fastening device, in particular a tab, may be associated with the side portion end to be fastened to the front or rear portion to form a closed position defining a leg opening.

For the open type of article, the connection member may advantageously be connected to the side portion end in combination with the attachment of the fastening device to the side portion end. For example, the joining of the fastening device to the side portion end may be made in the same production step as the joining of the connecting member to the side portion end.

In another variant, the article may be a pant-shaped article. Such an article is delivered as a closed, pant-like article, which is intended to be pulled up as regular underwear. In pant-like articles, the side portion ends of the front and rear portions of the article may be joined via side seams so as to form the closed position of the article defining a leg opening.

In a pant-shaped type of article, the connection member may advantageously be connected to the side portion end in combination with the formation of the side seam.

BRIEF DESCRIPTION OF THE DRAWINGS

In the following, the invention will be described with reference to non-limiting examples in the form of example embodiments, with reference to the enclosed drawings wherein.

DETAILED DESCRIPTION OF PREFERRED EMBODIMENTS

The invention will, in the following, be exemplified by embodiments. It is to be understood, however, that the embodiments are included in order to explain principles of the invention and not to limit the scope of the invention defined by the appended claims.

Figure 1:
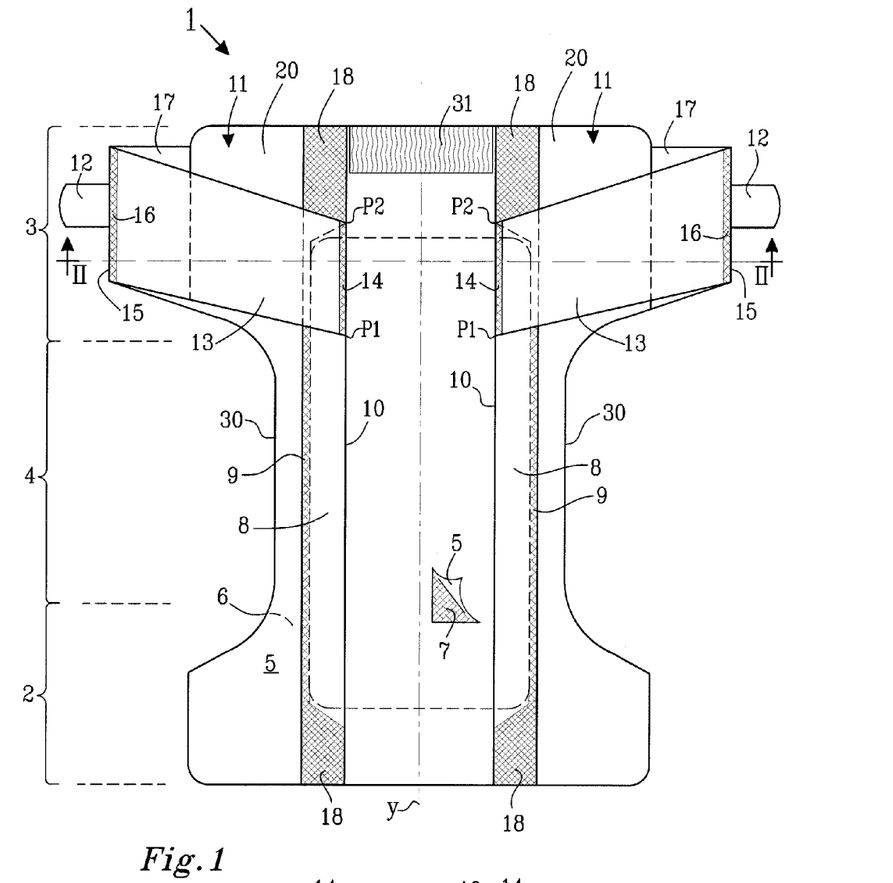
FIG. 1 is a top view of an absorbent article according to a first embodiment of the invention.

FIG. 1 illustrates schematically a disposable absorbent article 1, such as a diaper or incontinence guard, shown in an open flat position. The article 1 extends in a transverse direction x and in a longitudinal direction y. The article 1 includes a front portion 2 intended during use to be worn against the front part of the wearer's body, a rear portion 3 intended during use to be worn against the back of the wearer's body, and an intermediate crotch portion 4 located between the front 2 and rear 3 portions. When the article 1 is mounted to a wearer, parts of the longitudinal edges of the crotch portion 4 forms two leg openings 30, so that the crotch portion 4 during use will be located in the crotch region of the wearer.

Although not illustrated in FIG. 1, the leg openings 30 may advantageously be provided with elastically extensible regions so as to create a gusset around each leg when the article is worn.

The article 1 includes a liquid permeable top side, here in the form of a top sheet 5, a liquid impermeable back side, here in the form of a back sheet 6 and an absorbent body 7 enclosed between the top and back sheet.

The liquid permeable top sheet 5 can be composed of a nonwoven material, e g spunbond, meltblown, carded, hydroentangled, wetlaid etc. Suitable nonwoven materials can be composed of natural fibres, such as wood pulp or cotton fibres, manmade fibres, such as polyester, polyethylene, polypropylene, viscose etc. or from a mixture of natural and manmade fibres. The top sheet may further be composed of tow fibres, which may be bonded to each other in a bonding pattern, as e.g. disclosed in EP-A-1 035 818. Further examples of materials suitable for top sheets are porous foams, apertured plastic films etc. The materials suited as top sheets should be soft and non-irritating to the skin and intended to be readily penetrated by body fluid, e.g. urine. The top sheet may be different in different parts of the absorbent article.

The back sheet 6 can be preferably of a liquid impervious material, such as a thin plastic film, e.g. a polyethylene or polypropylene film, a nonwoven material coated with a liquid impervious material, a hydrophobic nonwoven material, which resists liquid penetration or a laminate including plastic films and nonwoven materials. The back sheet material may be breathable so as to allow vapour to escape from the absorbent body 7, while still preventing liquids from passing through the back sheet. Examples of breathable back sheet materials are porous polymeric films, nonwoven laminates from spunbond and meltblown layers, laminates from porous polymeric films and nonwovens.

The absorbent body 7 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent body. The thin absorbent bodies, which are common in for example baby diapers and incontinence guards, often include a compressed mixed or layered structure of cellulosic fluff pulp and superabsorbent. The size and absorbent capacity of the absorbent body may be varied to be suited for different uses such as for infants or for incontinent adults.

The absorbent body 7 may include one or more layers which may be selected to improve the handling of bodily waste. Such layers are designed to receive a large amount of liquid in a short space of time and distribute it evenly across the absorbent body. They may include so-called transfer, distribution, surge or acquisition layers, and are usually located between the top sheet 5 and the absorbent body 7. The absorbent body 7 is at least located in the crotch portion 4 of the article 1, and may also extend into the front and rear portions 2, 3.

The top sheet 5 and back sheet 6 may generally have a similar extension in the plane, while the absorbent body 7 may have an extension which is somewhat smaller. The top sheet 5 and back sheet 6 are joined to one another around the periphery of the absorbent body 7, so that the absorbent body 7 is enclosed within the envelope formed by the top sheet 5 and back sheet 6. The top sheet 5 and back sheet 6 may be joined to one another by any means common in the art, e.g. ultrasonic welding, thermal welding or gluing.

Moreover, the illustrated article 1 has a pair of barriers 8 which extend at least along the longitudinal sides of the crotch region 4. The term "barrier" is herein used for the material intended to form a barrier 8, even if the "barrier" sometimes may lie flat on the top sheet 5, and not stand up, in for example an absorbent article when folded to fit in a package. The purpose of the barrier is to function as a barrier against sideway leakage.

The barrier 8 has a proximal end 9 extending in the longitudinal direction of the article 1. The proximal end 9 is associated with the top sheet 5. The barrier 8 further has a distal end 10 also extending in the longitudinal direction of the article 1. In the illustrated embodiment, the barrier 8 is connected to the top sheet 5 along the proximal end 9 and in connection regions 18. The connection regions 18 have the purpose of initially holding the barrier 8 in a folded position. To this end, in the connection regions 18 the barriers 8 are connected to the topsheet via or adjacent to its distal end 10. The connection regions 18 are located at the longitudinal ends of the barrier 8. Between the connection regions 18, the distal end 10 forms a free edge. To be useful against sideway leakage, the free end of the barrier 8 shall preferably be erected from the top sheet 5, between the connection regions 18, when the article 1 is in use. Hence, it is desired that the majority of the length of the distal end 10 forms a free end. In particular embodiments, the free end extends over at least the crotch portion of the article.

Advantageously, as in the illustrated embodiment, the connection regions 18 in which the distal end 10 is connected to the top sheet are relatively small and located adjacent to the front and rear end of the article 18.

The article 1 of FIG. 1 is only schematically represented and many details not relevant for explaining the invention have been left out. It is for example common to provide the barrier 8 with barrier elastics, e.g. in the form of elastic yarns, which will improve the fit. Further, as mentioned previously, leg elastics may be provided along the leg openings 30, providing an additional hinder against sideway leakage.

In the illustrated embodiment, each of the longitudinal sides of the rear portion 3 of the article 1 is provided with a side portion 11. The side portion 11 is the portion of the article extending transversly from the proximal end 9 of the barrier 8 (or the longitudinal extension thereof) to the outer side portion end 15 which is to be attached to the front portion 2 of the article 1 when the article 1 is worn.

In the illustrated embodiment, the side portion 11 is elastic. To this end the side portion 11 may be made of an elastic material or with built-in elastics. In particular embodiments, as in the illustrated embodiment, the side portion 11 includes an elastic side panel 17 in order to improve the fit to the wearer's waist. Advantageously, the elastic side panel 17 may provide for the elasticity of the side portion 11, that is, the remainder of the side portion 11 may be less elastic than the side panel 17, and may even be essentially inelastic.

The rear portion 3 of the article is provided with a centrally located waist elastic 31, for improving the fit of the article. In this embodiment, the waist elastic 31 is confined to the area in between the proximal ends 9 of the barriers 8, and will hence not influence the elasticity of the side portions 11.

The embodiment illustrated in FIG. 1 is an open-type article which is delivered in an open position, to be closed only when attached around the waist of a wearer. Hence, when applied to a wearer, the side portion ends 15 of the rear portion 3 are intended to be fastened to the front portion 2 so as to form a closed position of the article 1. Thereby leg openings 30 will form around the legs of the wearer. In the illustrated embodiment, a fastening device 12, here in the form of a tab, is associated with the side portion end 15, and is intended for fastening the rear portion 3 to the front portion 2. The fastening device 12 may for example be one part of a hook and loop system or an adhesive tape. The front portion 2 may be provided with receiving means to receive the fastening means 12. In the illustrated embodiment, a connecting member 13 is provided to connect the barrier 8 with the side portion 11. When mounting the article 1 on a wearer by bringing the article 1 to a closed position, the side portions 11 will be subject to outward traction. Accordingly, the connecting member 13 will pull the free end of the barrier 8 outwards and upwards from the position it had while lying flat on the top sheet 5 in the open position. Accordingly, the connection member 13 will contribute to erecting the barrier 8 when the article is worn, and to maintain it in an upright position.

The connecting member 13 is connected to the barrier 8 at a first connection 14. In particular embodiments, the first connection 14 is located adjacent to the free edge of the distal end 10 of the barrier 8 and in more particular embodiments, at the free edge distal end 10 itself as illustrated, since this location maximises the effect of the transferred traction forces on the barrier 8. The first connection 14 may be formed by a joint between the connecting member 13 and the barrier 8, which joint may be formed using e.g. ultrasonic welding or heat welding, either continuous or intermittent, or by using an adhesive.

The other end of the connecting member 13 is connected via a second connection 16 to the side portion 11 at a location adjacent to the side portion end 15, or to the side portion end 15 itself, as illustrated. The connection may advantageously be formed by a joint between the connecting member 13 and the side portion 11, e.g. by ultrasonic welding or heat welding, either continuous or intermittent, or by using an adhesive. If a fastening means 12 is also arranged at the side portion 11, the fastening means 12 may be attached to the side portion 11 at the same location as the connecting member 13. Indeed, the fastening means 12, the connecting member 13 and the side portion 11 may be attached to each other by the same second connection 16, e.g. by a weld line.

The first connection 14 extends from a first position P1 to a second position P2, wherein the second position P2 is further away from the transverse axis x than the first position P1. In FIG. 1, the first position P1 is located adjacent to the leg opening 30. The second position P2 is located adjacent to fastening region 18, that is, at the beginning of the free end of the barrier 8.

It will be understood that the second position P2 could be located further away from the beginning of the free end of the barrier 8, for example if a less wide connection member 13 is used.

Even if the material forming the barrier 8 extends along the full longitudinal length of the article as in FIG. 1, it is common to attach the barrier 8 to the remainder of the article 1, so that the length of the free end of distal end 10 is less than the length of the article 1, by securing the barrier to the top sheet 5 adjacent to the distal end 10, in the connection regions 18 adjacent to the lateral ends of the article. Hence, the free edge of the distal end 10 will have a longitudinal beginning at the end of the connection regions 18.

In the illustrated embodiment, the connecting member 13 of FIG. 1 has an essentially rectangular shape. However, many different shapes are conceivable, such as narrowing, triangular with a blunt end, rhombic or parallelepiped or with curved lateral edges.

The transversal length of the connecting member 13 is in the embodiment of FIG. 1 chosen so that it is essentially equal to the transversal distance between the first and the second connections 14, 16, as measured along the side portion 11 when the article 1 is in its open position, and with the barrier 8 lying flat at the top sheet 5. Hence, also the connecting member 13 lies flat without wrinkles. This means that the article 1 has an essentially flat configuration when in its open position, which facilitates packing of the article 1 in a package. In this configuration, the distal end 10 of the barrier 8 is located between the longitudinal axis y and the proximal end 9 of the barrier 8.

Alternatively, the length of the connecting member 13 may be less than the transversal distance between the first and the second connections 14, 15 as measured along the side portion when the article 1 is in its open position. In that case, the side portion 11 or the connection member 13 may be folded in order to get a flat configuration which is easy to pack in a consumer package.

In the above, it is referred to the lengths of the parts when in a relaxed state, not being stretched or extended.

In the embodiment as illustrated in FIG. 1, the side portions 11 are elastic. In FIG. 1, the side portions 11 include two parts, a non-elastic part 20 and an elastic part 17. The non-elastic part 20 is formed by a portion of the overall structure for forming the absorbent article, and includes the topsheet 5 and the backsheet 6 of the article 1. The elastic part is formed by elastic side panels 17 being attached to the non-elastic part 20. The elastic side panels are elastic at least in the transversal direction.

Moreover, in the illustrated article, the connection members 13 are elastic, at least in the transversal direction. In a particular embodiment, also the barriers 8 are elastic.

With the illustrated embodiment it can be particularly preferred if the free edges of the distal ends 10 of the barriers 8 are elastic. This could be achieved e.g. by application of elastic threads adjacent to the free ends. In the illustrated article of FIG. 1, the side portions 11 and the connecting members 13 are located at the rear portion 3 of the article. Optionally, connecting members 13 may be located at the front portion 2 or at both the rear portion 3 and the front portion 2.

Figure 2:
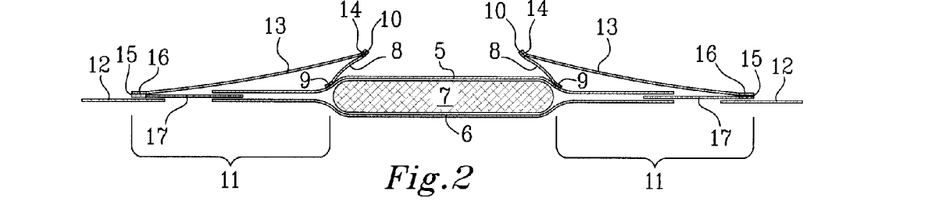
FIG. 2 is a cross-sectional view along a line II-II of FIG. 1.

FIG. 2 is a schematic cross-section of the rear portion 3 of the article 1 of FIG. 1 along the line II-II. However, in FIG. 2, the barriers 8 are illustrated as slightly erected, such as when the side portions 11 are subject to outward traction. The absorbent body 7 is enclosed by the top sheet 5 and the back sheet 6. The proximal end 9 of the barrier 8 is attached to the top sheet 5 and the distal end 10 of the barrier 8 is in an erected position, where the free edge of the distal end 10 is pulled outwards and upwards by the connecting member 13. The first connection 14 joins the connecting member 13 to the distal end 10 of the barrier 8. The connecting member 13 extends to the side portion end 15 of the side panel 11, where it is connected to the side panel 11 via the second connection 16. A fastening means 12 is attached to the side portion 11. In this embodiment, the fastening means 12 and the connecting member 13 are attached to the side portion 11 at essentially the same position. Alternatively, they may be attached at different positions. For example, the second connection 16 could be located at a distance from the side portion end 15, e.g. closer to the centre of the side portion 11.

However, if the side portion 11 is elastic or stretchable, it can be preferred that the second connection 16 is located at a position such that at least a part of the elasticity or strechability is located between the attachment of the proximal end 9 of the barrier 8 to the remains of the article, and the second connection 16. This ensures that at least some of the strechability or elasticity of the side portion will be efficient for moving the second connection, and hence act so as to pull the connecting member 13 when a traction force is applied to the side portion 11.

Hence, for an article which, as illustrated in FIG. 1, is provided with elastic side panels 17, it is desired that the second connection is positioned at the elastic side panel 17, in a particular embodiment, at a distance from the connection between the elastic side panel 17 and the non-elastic part 20 of the side portion 11.

Figure 3:
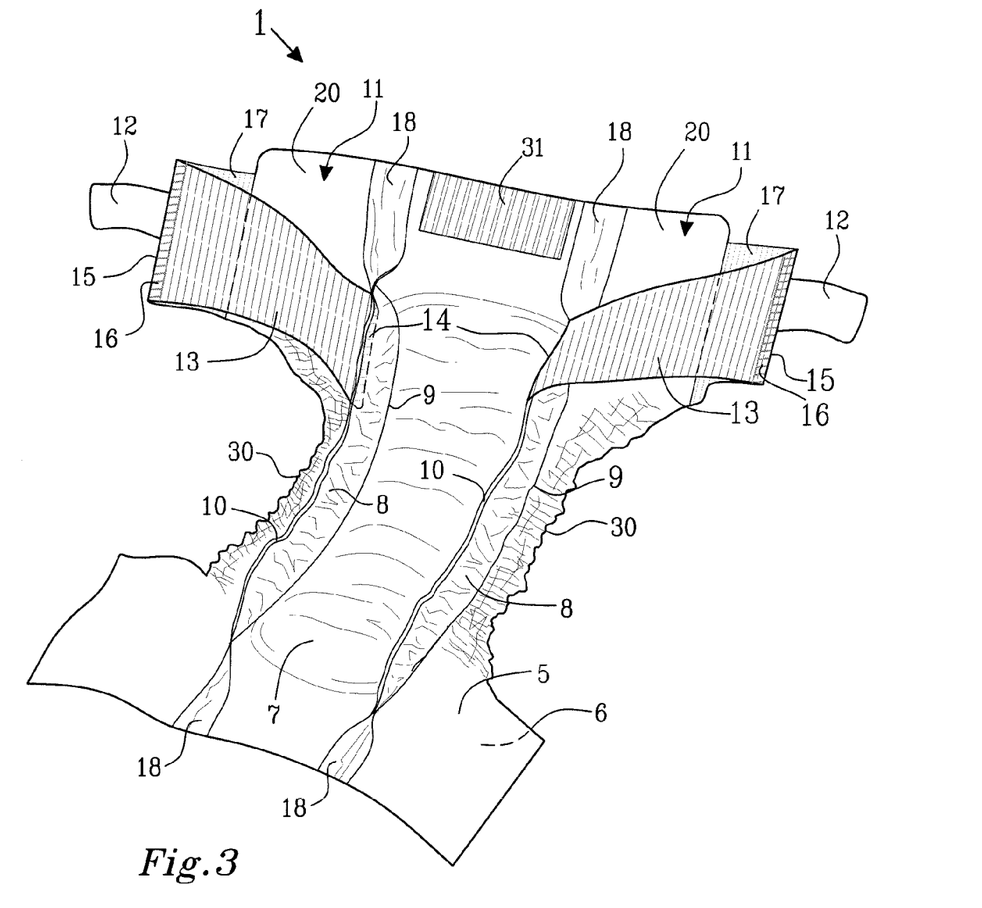
FIG. 3 is a perspective view of the absorbent article according to the embodiment of FIG. 1.

FIG. 3 is a perspective view of the embodiment of an article of FIGS. 1 and 2. Here, the barriers 8 are illustrated in an upright position, with the connecting members 13 pulling the free ends of the distal edges 10, as when the side portions 11 are subject to outward traction forces.

In FIG. 3, the leg openings 30 are illustrated as being provided with elasticised portions extending transversally outwardly of the barriers 8, at least in the crotch region, for forming a first hinder against leakage around the legs when the article is worn. In such embodiments, the barriers 8 will form a second hinder against leakage, which may complement the first.

Figure 4:
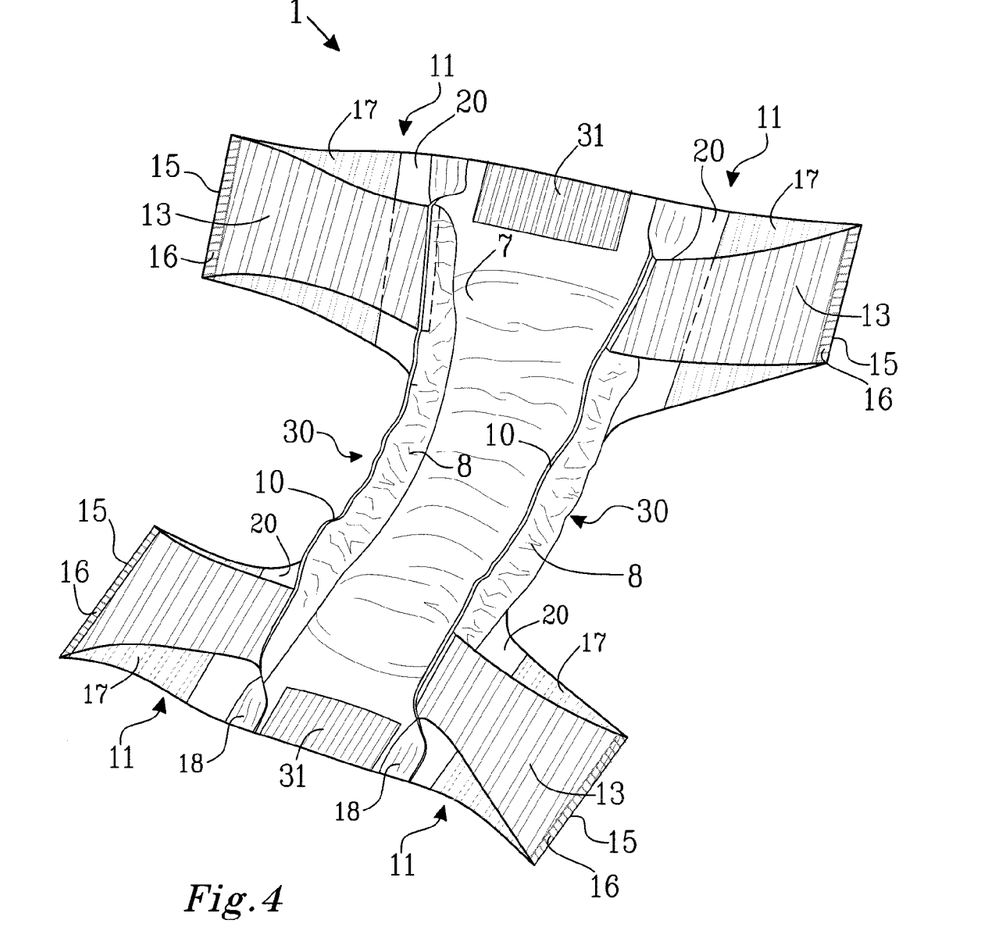
FIG. 4 is a perspective view of an absorbent article according to a second embodiment of the invention.

FIG. 4 illustrates a second embodiment of the invention, where the article 1 is a pant-shaped article. In FIG. 4, the article has been opened along the side seams for better visibility.

In the article 1 illustrated in FIG. 4, both the front 2 and the rear 3 portions of the article is provided with side portions 11. Connecting members 13 are attached at each of the side portions 11 via second connections 16 at the outer side edges 15 thereof. In this embodiment, it is understood that the second connections 16 could advantageously be formed in connection with the side seams for joining the front 2 and rear 3 portions of the article. Hence, the two side seams could be used to form the four second connections 16. The connecting members 13 are attached to the free edges of the distal ends 10 of the two longitudinally extending barriers 8 via first connections 14.

In the illustrated article, the leg openings 30 will be secured against leakage by the barrier 8, which will form the portion of the leg opening which is adjacent to the crotch of the wearer, and the side portions 11, which will form the portion of the leg opening on the outside of the leg. Accordingly, the barriers 8 and the side portions 11 (of both the front and the rear portion of the article) contribute to forming a comfortable seal around the leg opening 30 when the article is in a closed position.

However, alternative pant-shaped articles are naturally possible, for example where the leg openings are provided with elasticised portions extending transversally outwardly of the barriers 8, at least in the crotch region, for forming a first hinder against leakage around the legs when the article is worn. In such embodiments, the barriers 8 will form a second hinder against leakage, which may complement the first.

Figure 5:
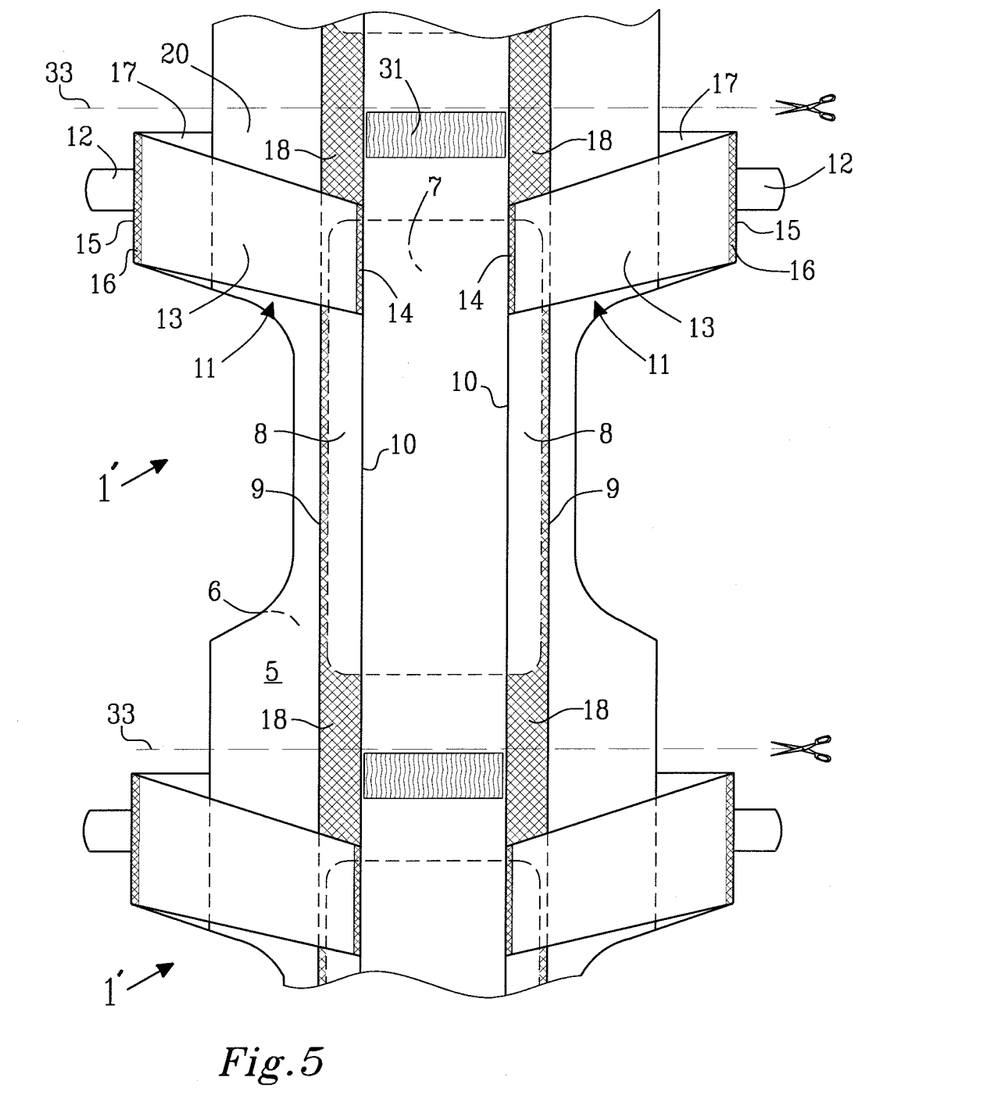
FIG. 5 illustrates a step in an embodiment of a method for manufacturing of an open-type absorbent article as described in relation to FIGS. 1-3.

FIG. 5 illustrates a step in the production of open-type absorbent articles, for example the articles illustrated in FIGS. 1-3. Article chassis 1' are formed in line one after the other, and are interconnected at their longitudinal ends. The chassis 1' are provided with barriers 8 along their longitudinal sides or at least in their crotch regions 4.

The method includes the attachment of a connecting member 13 so as to connect the barrier 8 with the side portion 11, by forming a first connection 14 between the connection member 13 and the barrier 8, first connection 14 being located at a distance from the proximal end 9 of the barrier 8, and a second connection 16 between the connection member 13 and the side portion 11.

Many options are available for forming the first and second connections 14, 16. For example, the first connection 14 may be formed between the connection member 13 and the barrier 8 before the attachment of the barrier 8 to the chassis 1'.

In a later production step, each chassis 1' may be separated from the consecutive chassis 1' along a pre-determined separation line 33, such that separate articles 1 are formed.

Figure 6:
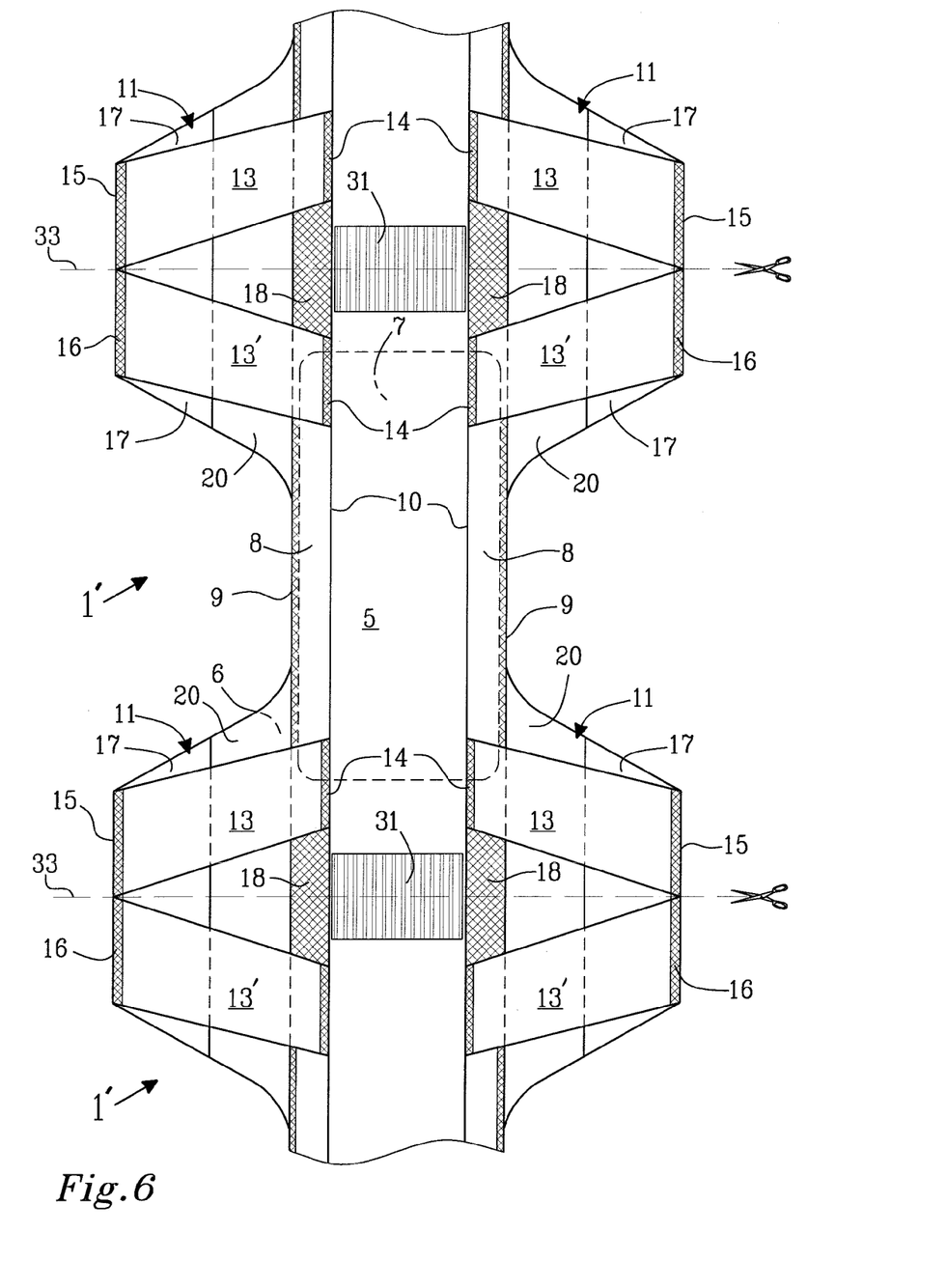
FIG. 6 illustrates a step in an embodiment of a method for manufacturing a pant-shaped absorbent article as described in relation to FIG. 4.

FIG. 6 illustrates a step in the production of absorbent articles with connecting members 13 at both the front 2 and rear 3 portions. This configuration would be suitable for both open-type and pant-type absorbent articles, even if FIG. 6 displays an embodiment intended for pant-type articles. Elastic materials 13, 13' are attached to the barriers 8 via a first connections 14. The other end of the connection member 13 is attached to the side portion 11 as its end 15, via a second connection 16.

Again, numerous alternatives are possible for forming the connections 14, 16. For example, connections may be formed extending over two consecutive chassis 1', so as to attach the connection members 13' of the front region of one chassis 1' and the connection members 13' of the rear regions of the consecutive chassis 1' in one step.

For forming pant-shaped articles, regardless of which method of the ones described above is used, the front and rear portions of the articles should be joined via side seams. The side seams may advantageously be formed before the individual articles are separated from each other.

The second connection between the connection member 13 and the side portion 11 may be formed in combination with the side seams.

In the illustrated embodiments, the barrier 8 is located along the longitudinal sides of the article 1. In this position the barrier is helpful in preventing sideways leakage, for example at the leg openings. A similar additional barrier may also be used along the lateral ends of the absorbent body 7 or adjacent to the lateral ends of the article 1, helpful in preventing leakage along the wearers back and/or stomach. If using such an additional barrier, it may be arranged to have a corresponding connecting member as described above, in order to promote dragging out of the barrier.

The invention has been described above by way of examples only and the skilled person will appreciate that many modifications of the above-described embodiments are conceivable within the scope of the appended claims.

In particular, it should be understood that features as described in the above with reference to different embodiments may be combined. In particular, features described with reference to an open-type article may be equally applicable to a pant-shaped article, and vice-versa.

In the illustrated examples, the connection member is formed by a single piece of material, which may be preferred for simplicity. However, the connection member may be formed out of several parts, which cooperate to transfer a traction force from the side portion to the barrier, so as to promote drawing out of the barrier.

The invention claimed is:

1. A disposable absorbent article intended to be worn around the waist of a user and extending in a longitudinal direction about a longitudinal axis and in a transverse direction about a transverse axis, the article comprising:
    a front portion,
    a rear portion,
    an intermediate crotch portion,
    a side portion extending transversely outwardly from said front or rear portion,
    an elastic side panel attached to an outwardly transverse end of the side portion,
    a liquid-permeable top side,
    a liquid-impermeable back side, and
    a barrier extending along a longitudinal side of said crotch portion, the barrier comprising:
        a proximal end extending in said longitudinal direction, said proximal end being connected to the remains of the article and
        a distal end extending in said longitudinal direction, said distal end forming a longitudinally extending free edge,
    wherein a connecting member connects the barrier with said elastic side panel by extending between
    a first connection where the connecting member is connected to the barrier, the first connection being located at a distance from the proximal end of the barrier, and
    a second connection where the connecting member is connected to the elastic side panel such that when said elastic side panel is subject to a traction force said traction force will be at least partially transferred to the barrier via said connecting member.

2. The disposable article according to claim 1, wherein said first connection between the barrier and the connecting member is located closer to the distal end than to the proximal end of the barrier.

3. The disposable article according to claim 2, wherein the first connection is located at the free edge formed by said distal end.

4. The disposable article according to claim 1, wherein the side portion is stretchable.

5. The disposable article according to claim 1, wherein said connecting member is stretchable.

6. The disposable article according to claim 1, wherein at least the free edge of the distal end of said barrier is stretchable.

7. The disposable article according to claim 1, wherein the size and stretchability of the connecting member are related to the size and stretchability of the elastic side panel such that, when the elastic side panel is subject to the traction force both the elastic side panel and the connecting member are drawn out by said traction force.

8. The disposable article according to claim 1, wherein the first connection between the barrier and the connecting member extends longitudinally from a first position to a second position, said second position being located further away from the transverse axis than the first position.

9. The disposable article according to claim 8, wherein said first position is located adjacent to a leg opening of the article formed when the front and rear portions are fastened to each other.

10. The disposable article according to claim 8, wherein the second position is located adjacent to a longitudinal beginning of the free end of the barrier.

11. The disposable article according to claim 1, wherein, when the article is in a storage position before application of the traction force to the elastic side panel, the distal end of the barrier is located between the longitudinal axis of the article and the longitudinal proximal end of the barrier.

12. The disposable article according to claim 1, wherein the article is provided with two barriers extending longitudinally along transversely opposite sides of the crotch portion, and wherein the rear or front portion is provided with an additional side portion and elastic side panel, wherein each of the elastic side panels is attached to the outwardly transverse end of the respective side portion provided on transversely opposite sides of said rear or front portion, and wherein two connecting members are provided to connect each barrier with the respective elastic side panel.

13. The disposable article according to claim 1, wherein the article is provided with two barriers extending longitudinally along transversely opposite sides of the crotch portion, and wherein the article is provided with an additional three side portions and elastic side panels, each of the elastic side panels attached to the outwardly transverse end of the respective side portion, and the rear portion and the front portion are each provided with two of the side portions and elastic side panels, and with two connecting members, such that each one of the two barriers is connected to one elastic side panel at the rear portion of the article via one connecting member, and to another elastic side panel at the front portion of the article via the other connecting member.

14. The disposable article according to claim 1, wherein the article is an open-type article, and a fastening device is associated with an outwardly transverse end of the elastic side panel for releasably fastening said outwardly transverse end of the elastic side panel to the front or rear portion to form a closed position of the article defining a leg opening.

15. The disposable article according to claim 14, wherein the second connection is formed in combination with the attachment of said fastening device to the outwardly transverse end of the elastic side panel.

16. The disposable article according to claim 15, wherein the second connection joins together the connecting member, the fastening device, and the outwardly transverse end of the elastic side panel.

17. The disposable article according to claim 1, wherein the article is pant-shaped, the front and rear portion being interconnected via longitudinal side seams such that the article forms a closed position defining a leg opening, and wherein an outwardly transverse end of the elastic side panel is joined to one of said side seams.

18. The disposable article according to claim 17, wherein the second connection is formed in combination with one of said side seams.

19. The disposable article according to claim 1, wherein the second connection is located at an outwardly transverse end of the elastic side panel.

20. The disposable article according to claim 1, wherein the second connection is located closer to an outwardly transverse end of the elastic side panel than to the proximal end of the barrier.

* * * * *